(12) United States Patent
Katoh et al.

(10) Patent No.: US 7,958,894 B2
(45) Date of Patent: Jun. 14, 2011

(54) DRAPE FOR CLEAN OPERATION

(75) Inventors: Osamu Katoh, Toyohasi (JP); Masao Horie, Osaka (JP); Yoshihiko Sano, Osaka (JP); Yasushi Ohyama, Osaka (JP); Norihiko Furuta, Osaka (JP)

(73) Assignees: Osamu Katoh, Toyohashi-shi, Aichi (JP); Nipro Corporation, Osaka-shi, Osaka (JP)

( * ) Notice: Subject to any disclaimer, the term of this patent is extended or adjusted under 35 U.S.C. 154(b) by 707 days.

(21) Appl. No.: 11/887,237

(22) PCT Filed: Mar. 27, 2006

(86) PCT No.: PCT/JP2006/306150
§ 371 (c)(1),
(2), (4) Date: Sep. 27, 2007

(87) PCT Pub. No.: WO2006/104093
PCT Pub. Date: Oct. 5, 2006

(65) Prior Publication Data
US 2009/0241970 A1    Oct. 1, 2009

(30) Foreign Application Priority Data

Mar. 28, 2005 (JP) .................................. 2005-092961
Aug. 16, 2005 (JP) .................................. 2005-236170

(51) Int. Cl.
*A61B 19/00*     (2006.01)
(52) U.S. Cl. ........................................ 128/849; 128/853

(58) Field of Classification Search .................. 128/845, 128/849–856; 600/21
See application file for complete search history.

(56) References Cited

U.S. PATENT DOCUMENTS

| 4,367,728 A | * | 1/1983 | Mutke .............................. 600/21 |
| 5,316,541 A | * | 5/1994 | Fischer ............................ 600/21 |
| 5,824,161 A | * | 10/1998 | Atkinson ............................ 134/6 |
| 2004/0116770 A1 | | 6/2004 | O'Connor et al. |

FOREIGN PATENT DOCUMENTS

| JP | 39-13989 | 7/1964 |
| JP | 44-23307 | 10/1969 |
| JP | 45-40515 | 12/1970 |
| JP | 2000-24057 A | 1/2000 |

* cited by examiner

*Primary Examiner* — Michael A. Brown
(74) *Attorney, Agent, or Firm* — Birch, Stewart, Kolasch & Birch, LLP

(57) ABSTRACT

A drape for clean operation is a flexible bag-shaped structure for maintaining a substantially closed operating space around an operation site. The bag-shaped structure comprises a bottom wall 1 and a transparent top wall 2 and has a closed proximal end 100*a* and a closed distal end 100*b*. The bottom wall 1 is provided with at least one operation site-revealing opening 3 close to the proximal end, and the top wall 2 is provided with at least one pair of hand insertion parts 4 at a position close to the operation site-revealing opening 3 to allow the physician to aseptically insert the hands into the operating space, and a closed, openable and closable medical device supply port 5 for supplying medical devices required for operations at a position away from the operation site-revealing opening 3.

12 Claims, 6 Drawing Sheets

DRAPE FOR CLEAN OPERATION

TECHNICAL FIELD

The present invention relates to a drape for clean operation. The drape for clean operation is a medical device designed to maintain a substantially closed space around an operation site to allow the physician to perform an aseptic operation within the closed space, and used for avoidance of physician's contamination and bedside contamination by the blood.

BACKGROUND ART

Up to now, surgical operations in operating rooms and catheter diagnosis or treatments in angiographic imaging rooms are performed in an environment that takes into account the protection of patients against bacterial infection.

However, it is difficult to say that such an environment includes sufficient consideration of the physician's risks of infection caused by blood bled from the operative field or punctured site of the vessel. Thus, the physicians are obliged to perform operations in an environment where they are exposed to the risk of blood infection. Even in the conventional practice, the physician's risk of infection has been somewhat avoided by use of operating gowns and masks. However, these goods are designed for the main purpose of protection of the patients and are insufficient for avoidance of the physician's risk of infection.

Accordingly, there are eager desires for supply of a device that enables to avoid the physician's risks of blood infection easily and completely without decreasing the freedom of the surgical procedure. On the other hand, the treatments involving surgical operations will have problems associated with the bedside contamination caused by the blood.

DISCLOSURE OF INVENTION

Problems to be Solved by the Invention

The present invention has been made in view of the above circumstances and is intended to provide a drape for clean operation designed to provide a substantially closed space, which enables to perform an aseptic operation as well as to prevent both the bedside contamination and the physician's risk of infection caused by the blood.

Means for Solving the Problems

The drape for clean operation of the present invention is a flexible bag-shaped structure for maintaining a substantially closed operating space around an operation site, said bag-shaped structure comprising a bottom wall and a transparent top wall and having closed proximal and distal ends, characterized in that said bottom wall is provided with at least one operation site-revealing opening close to the proximal end, that said top wall is provided with at least one pair of hand insertion parts for allowing the physician to insert the hands aseptically into the operating space at a position close to the operation site-revealing opening, and that said top wall is further provided with a closed, openable and closable medical device supply port for supplying medical devices required for operations, at a position away from said operation site-revealing opening.

In one embodiment of the present invention, the drape for clean operation has a closed proximal end and a closed distal end and the bottom wall is provided with two openings for revealing the patient's operation site close to the proximal end of the bag-shaped structure. The top wall is provided with a pair of hand insertion parts for physician, which allow the physician to insert the hands aseptically into the operating space, at a position close to the operation site-revealing opening on one side of the top wall with respect to the longitudinal axis of the bag-shaped structure. The top wall is further provided with a pair of hand insertion parts for assistant, which allow the assistant to insert the hands aseptically into the operating space, at a position close to the physician's hand insertion parts on the distal side of the bag-shaped structure.

In another embodiment of the present invention, the bag-shaped structure has a closed proximal end and a closed distal end and the bottom wall is provided with an opening for revealing an operation site of a patient close to the proximal end of the bag-shaped structure. On the other hand, the top wall is provided with a pair of physician's hand insertion parts, which allow the physician to insert the hands aseptically into the operating space, close to the operation site-revealing opening. The top wall is further provided with a closed, medical device supply port for supplying medical devices required for operations, at a position away from said operation site-revealing opening.

Preferably, sealing means, which adhere tightly to the region surrounding the operation site, is provided around a peripheral portion of the operation site-revealing opening to prevent displacement of the operation site-revealing opening with respect to the operation site, leakage of the blood or the like from the operating space and inflow of the open air into the operating space. In this case, it is preferred that the sealing means is an adhesive tape.

Further, each of the hand insertion parts is formed into a glove box comprising an arm-covering sheath and a glove-shaped hand-covering sheath. At least the hand-covering sheath in itself has good lubricating property and includes digit-covering sheaths so designed as to have a length that allows the digit-covering sheaths to be easily broken at the distal end thereof by insertion of each digit to expose the physician's digits to the space sufficiently after digit-covering sheaths are broken. A pair of hand insertion parts may be provided adjacently and fusion-bonded at the adjoining parts thereof located at the opening of the proximal end of the hand insertion parts. Also, there may be provided physician's hand insertion parts and assistant's hand insertion parts adjacently, which are fusion-bonded each other at the adjoining parts thereof located at the opening of the proximal end of the hand insertion parts.

The top wall may be provided with a disposal bag on the opposite side of the longitudinal axis of the top wall from the physician's hand insertion parts. The top wall may be provided with a closable opening for installation of gloves at an intermediate position between the location of the disposal bag and that of the hand insertion parts. The top wall may be further provided with an insertion port for contrast agent/fluid replacement feeding line, an intravascular echography probe-loading port and a chemical delivery port on the opposite side of the longitudinal axis of the top wall from the assistant's hand insertion parts.

The medical device supply port may be reinforced by a reinforcement material to keep the open state of the medical device supply port during supplying a medical device.

The top wall may be provided with means for fixing it to hanging means so that the top wall and the bottom wall create a space between them when the fixing means is fixed to the hanging means.

The present invention has been described in general form as above, but further understanding will be provided by referring to some specific embodiments of the present invention.

However, these embodiments are given by way of illustration only and thus are not limitative of the present invention unless otherwise stated.

Effects of the Invention

According to the present invention, there would be provided the following advantages: Physicians can perform manipulations such as operations, diagnoses and treatments in a closed space substantially separated from the physicians, thus making it possible to prevent the bedside contamination and the physician's risk of infection caused by the blood. It is possible to maintain the operative field or punctured site of the vessel in a clean environment, thus making it possible to reduce the patient's risk of infection markedly. It eliminates the use of conventionally required operating gowns, masks and drapes, the present invention is more cost efficient than the conventional procedures. Further, the drape of the present invention is substantially composed chiefly of wall sheets, so that it is lightweight, easily foldable and easy of disposal after use.

DESCRIPTION OF SYMBOLS

Figure 1:
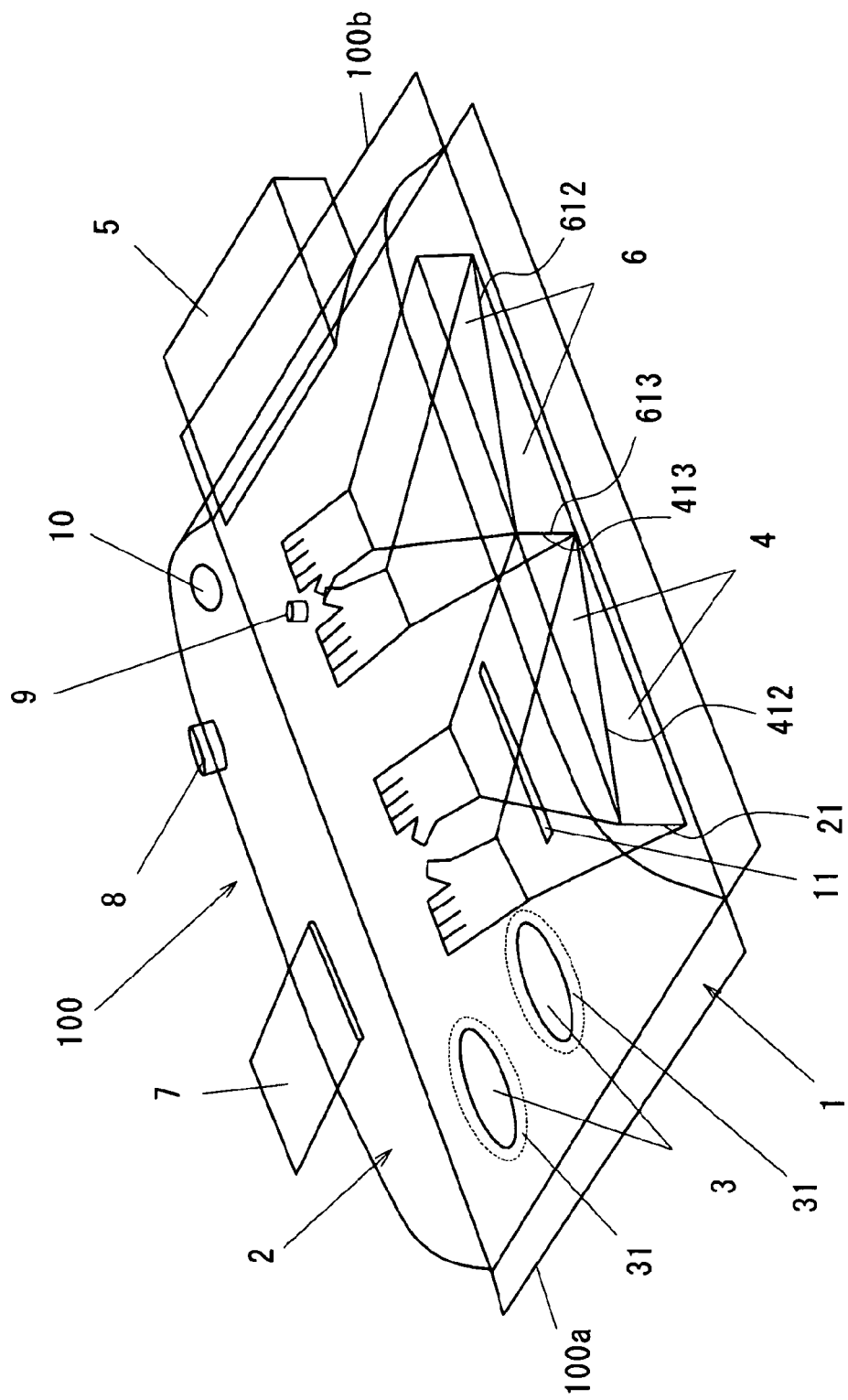
FIG. 1 is a perspective view of a drape for clean operation according to one embodiment of the present invention.

1: bottom wall
2: top wall
3: operation site-revealing opening
4 hand insertion parts for physician
41 arm-covering sheath
411 opening
412 adjoining part
413 adjoining part
42 hand-covering sheath
43 digit-covering sheath
5 medical device supply port
51 opening
52 reinforcement material
53 fastener
6 hand insertion parts for assistant
61 arm-covering sheath
612 adjoining part
613 adjoining part
62 hand-covering sheath
63 digit-covering sheath
611 opening
7 disposal bag
8 insertion port for contrast agent/fluid replacement feeding line
9 chemical delivery port
10 intravascular echography probe-loading port
11 glove installation port
12 attaching means for attachment to hanging means
13 hanging means (pole)

BEST MODE FOR CARRYING OUT THE INVENTION

A drape for clean operation of the present invention is a flexible bag-shaped structure for providing and maintaining a substantially closed operating space around an operation site in use, said bag-shaped structure comprising a bottom wall and a transparent top wall and having closed proximal and distal ends. The bottom wall is provided with at least one operation site-revealing opening. On the other hand, the top wall is provided with at least one pair of physician's hand insertion parts, which allow the physician to aseptically insert the hands into the operating space and approach the operation site-revealing opening, close to the operation site-revealing opening. Further, the top wall is provided with and a closed, openable and closable medical device supply port for supplying medical devices required for an operation at a position away from the operation site-revealing opening.

Around the peripheral part of operation site-revealing opening, there is provided adhesive tape which adheres to the surrounding of the operation site. The hand insertion parts are made into a glove box including an arm-covering sheath and a glove-shaped hand-covering sheath. The hand-covering sheath includes digit-covering sheaths so designed as to have a length that allows the digit-covering sheaths to be easily broken at the distal ends thereof by insertion of each digit and sufficiently expose the physician's digits to the space after breakage.

The top wall is provided with a disposal bag on the opposite side of the longitudinal axis of the top wall from the physician's hand insertion parts, and a closable opening for installation of a glove at an intermediate position between the location of the disposal bag and that of the hand insertion parts.

The top wall is provided with an insertion port for contrast agent/fluid replacement feeding line, an intravascular echography probe-loading port and a chemical delivery port on the opposite side of the longitudinal axis of the top wall from the assistant's hand insertion parts.

The medical device supply port is reinforced with a reinforcement material to keep the open state of the medical device supply port during supplying medical devices.

Embodiment 1

Figure 2:
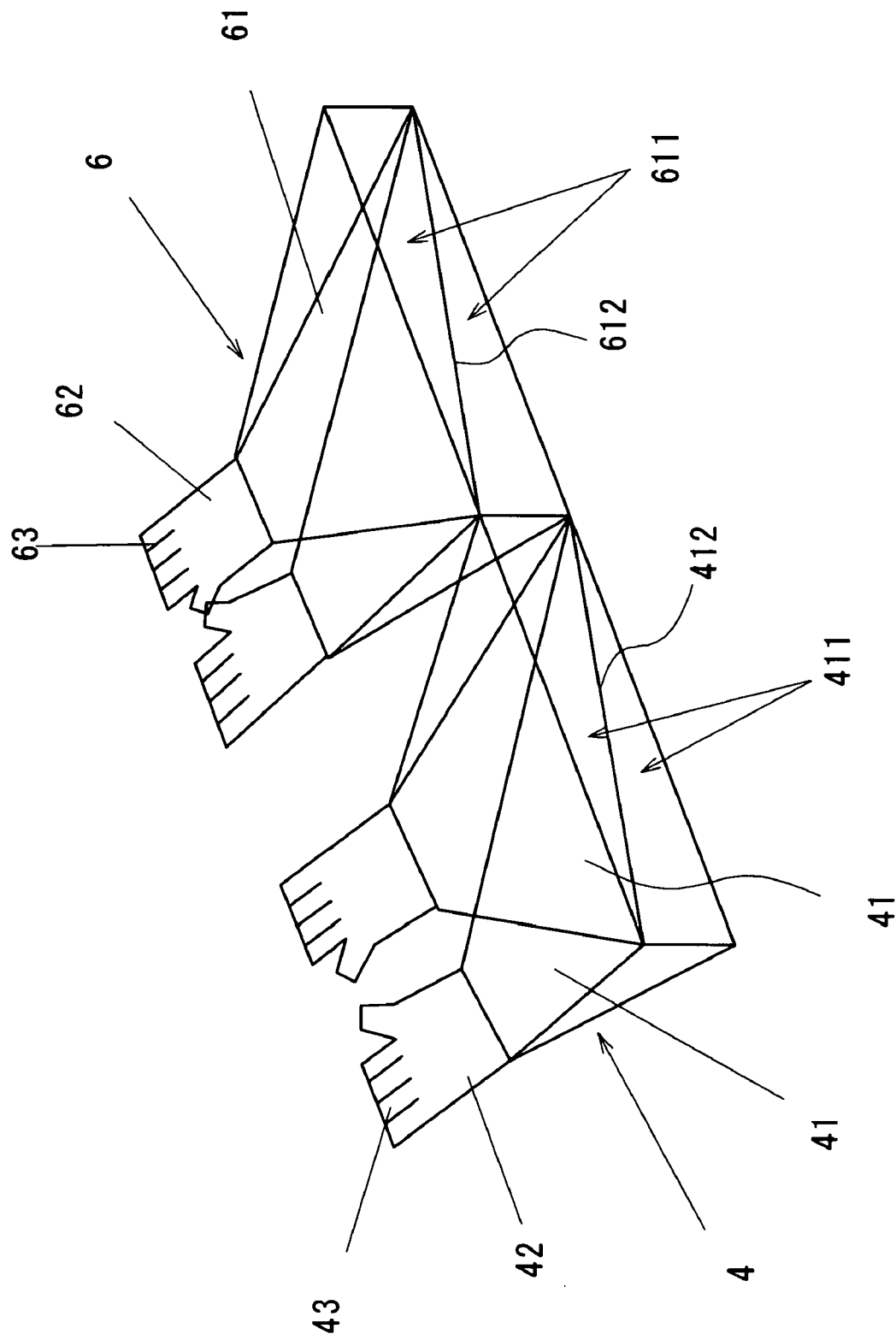
FIG. 2 is an explanatory diagram of hand insertion parts shown in FIG. 1.
Figure 3:
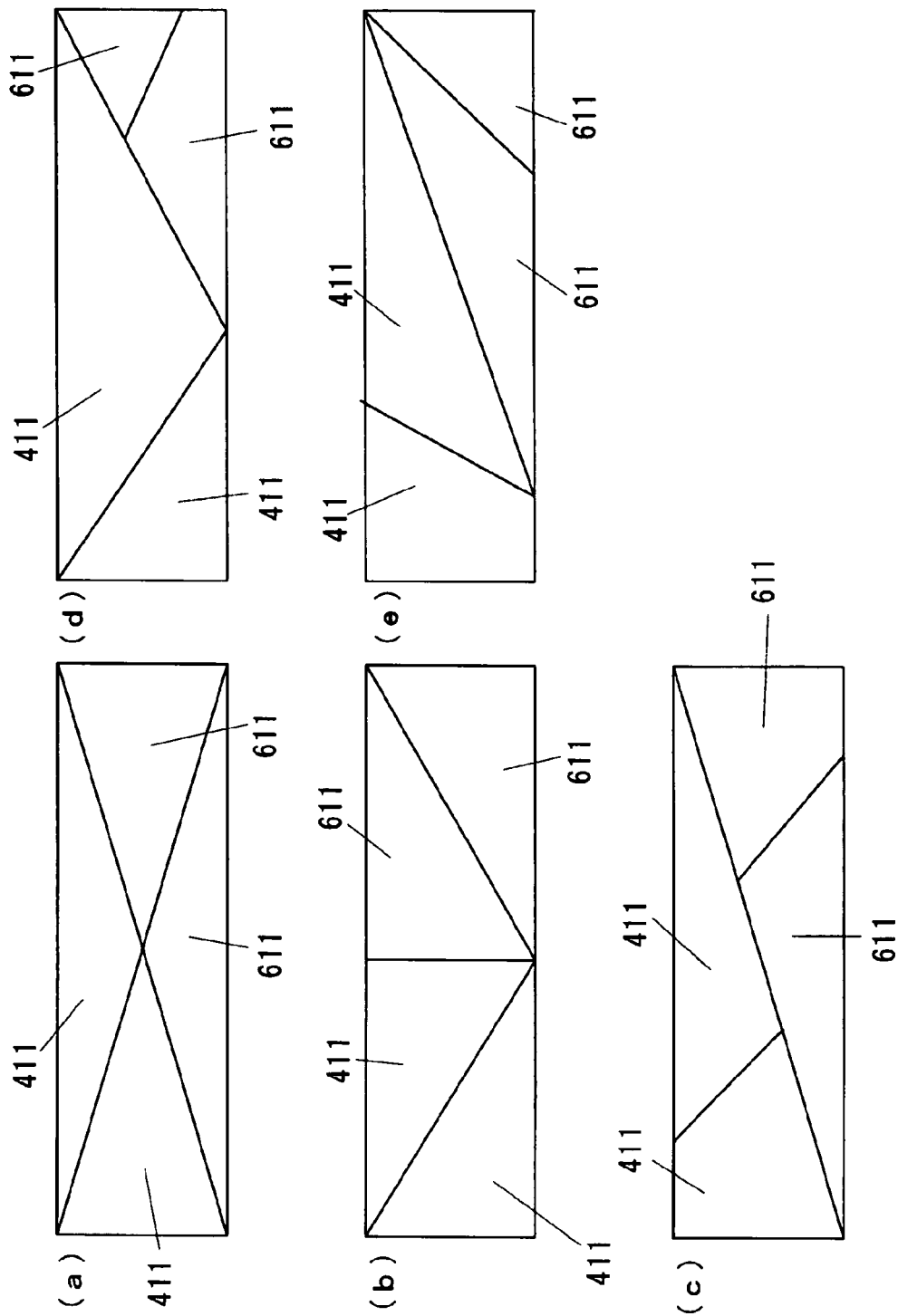
FIG. 3 is an explanatory diagram illustrating openings (patterns of the opening) of the hand insertion parts.
Figure 4:
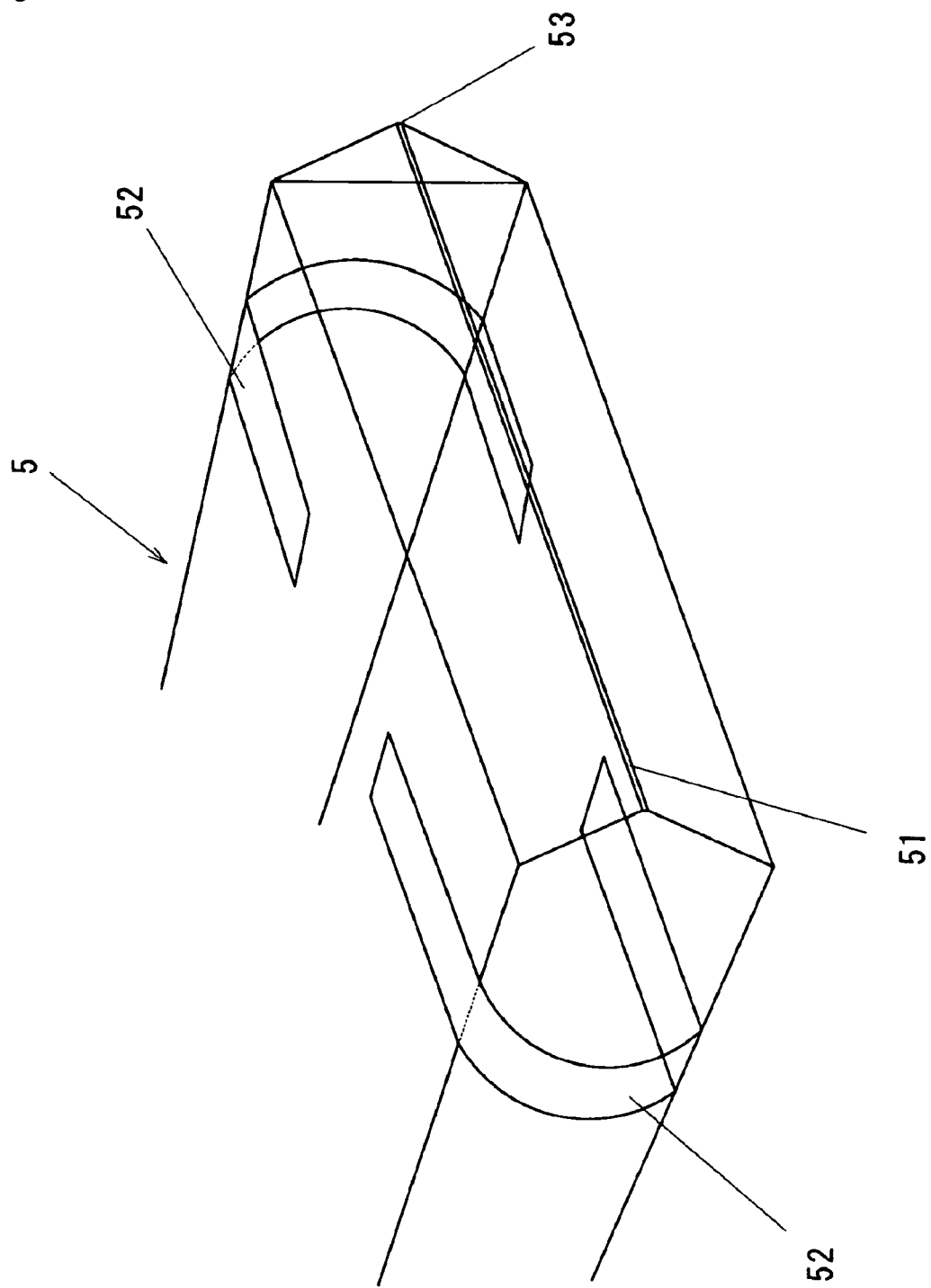
FIG. 4 is a diagram illustrating medical device supply port reinforced by reinforcement materials.

FIG. 1 is a perspective view of a drape for clean operation according to one embodiment of the present invention, and FIG. 2 is an explanatory diagram of physician's hand insertion parts shown in FIG. 1. FIG. 3 is an explanatory diagram illustrating some embodiments of the hand insertion parts (which illustrate patterns of the opening on the proximal end), and FIG. 4 is a diagram illustrating medical device supply port reinforced by a reinforcement material.

As illustrated in FIG. 1, a drape 100 for clean operation of Embodiment 1 is a flexible bag-shaped structure for maintaining a substantially closed operating space around an operation site in use. The bag-shaped structure comprises a bottom wall 1 and a transparent top wall 2, and has a closed proximal end 100a and a closed distal end 100b. The bottom wall 1 is shaped into a rectangular form and provided with two operation site-revealing openings 3 close to the proximal end 100a of the drape 100. The top wall 2 is provided with a pair of physician's hand insertion parts 4 close to the operation site-revealing opening 3 on one side of the longitudinal axis of the drape 100. Close to the physician's hand insertion parts 4 there is provided a pair of assistant's hand insertion parts 6 on the side of the distal end of the drape. On the side of the distal end 100b of the drape 100, the drape 100 is provided with an openable and closable medical device supply port 5 for supplying medical devices required for an operation. The medical device supply port 5 is normally being closed. The top wall 2 is bonded to the bottom wall 1 by adhesion or fusion welding and, in use, forms and maintains a substantially closed operating space, which surrounds and encloses an upper part of the bottom wall 1.

A plastic material for bottom wall 1 and top wall 2 or a sheet for walls is a film or flexible thin sheet made of transparent plastic material such as polyethylene, polyester, plasticized polyvinyl chloride and polyamides. The bottom wall 1 is preferably made into opaque to make the operation site invisible.

The bottom wall 1 is provided with an adhesive tape 31, which adheres to the surrounding of the operation site, at the peripheral part of the operation site-revealing opening 3 on the side of an outer surface of the bottom wall. This makes it possible to prevent displacement of the operation site-revealing opening with respect to the operation site, leakage of the blood or the like from the operating space at the time of bleeding by operation, and inflow of the open air into the operating space. The bottom wall 1 may be provided with hook and pile-fastening tapes (not illustrated in the drawings), for example, MAGIC TAPE (Registered trademark), which enables to fix the bottom wall 1 to an auxiliary table for surgical operation. The bottom wall 1 may be provided with a drain hole (not illustrated in the drawings) close to the edge on the distal end.

The medical device supply port 5 is capable of being used as a supply port 5 for supplying medical devices such as trays, guide wires or the like. The medical device supply port 5 may be used only for supplying and out the trays and guide wires. In this case, the top wall is provided with ports for supplying other medical devices, such as an insertion port 8 for contrast agent/fluid replacement feeding line, a chemical delivery port 9 and an intravascular echography probe-loading port 10 as occasion demands. These ports, i.e., insertion port 8, chemical delivery port 9 and intravascular echography probe-loading port 10 have a closable structure and are formed on the opposite side of the longitudinal axis of the top wall 2 from the located site of the proximal end of the assistant's hand insertion parts 6. As shown in FIG. 4, the medical device supply port 5 is provided with a fastener 53 to close the opening 51 of the medical device supply port 5 and reinforced by a reinforcement material 52 to maintain the medical device supply port when the fastener 53 is opened to carry in the medical devices.

The physician's hand insertion parts 4 is provided in the top wall 2 at a position close to the operation site-revealing opening 3 of the top wall 2 in order to allow the physician's hand to reach the operation site.

As illustrated in FIG. 2, the hand insertion parts 4 are arranged in pairs and assembled into a glove box. Each hand insertion part 4 comprises an arm-covering sheath 41 located on the side of the proximal end thereof and a glove-shaped hand-covering sheath 42 located on the side of the distal end thereof. At least the hand-covering sheath 42 is generally made of a plastic material, which has good lubricating property by itself, such as polyethylene, polyamide, polytetrafluoroethylene and the like. The hand-covering sheath 42 includes digit-covering sheaths 43 which are so designed as to have a length that allows the digit-covering sheaths 43 to be easily broken at the distal end thereof by insertion of each digit and sufficiently expose the physician's digits to the space after being broken. The hand-covering sheath 42 may be improved in lubricating property by applying silicone oil to an outer surface of the hand-covering sheath 42.

The paired physician's hand insertion parts 4, 4 are arranged adjacent to each other and fusion-bonded at adjoining parts 412 of the openings 411 on the proximal ends thereof to keep the sealing performance of the drape. The remaining parts of the openings 411 are fusion-bonded to the periphery of the opening 21 provided in the top wall 2. Further, the assistant's hand insertion parts 6 are arranged in pairs and constructed in the same manner as the physician's hand insertion parts 4. Thus, the details of the assistant's hand insertion parts 6 are omitted to avoid repetition of the description.

The physician's hand insertion parts 4 and the assistant's hand insertion parts 6 are located adjacently and fusion-bonded together at the adjoining parts 413, 613 of openings 411, 611 of the proximal end of the hand insertion parts 4, 6. The opening patterns for the physician's hand insertion parts 4 and the assistant's hand insertion parts 6 may have any opening pattern of FIG. 3, in place of the opening pattern shown in FIG. 2. In any of the patterns, the hand insertion parts are so designed that the left hand is located at the level equal to or below that of the right hand.

The top wall 2 is provided with a disposal bag 7 on the opposite side of the longitudinal axis thereof from the opening 411 located at the proximal end of the physician's hand insertion parts 4. In an intermediate portion of the top wall between the installation site of the disposal bag and that of the physician's hand insertion parts, there is provided a closable opening 11 for installation of a glove, which allows the physician to put the hands out of the space to replace the glove with new one if need be during operation.

The above drape is easy to manufacture since it mainly comprises the bottom wall 1 and top wall 2. It enables to fix the hand insertion parts 4, 6 to the top wall 2 certainly and air-tightly since the hand insertion parts 4, 6 can be easily fusion-bonded to the top wall 2 when they are made of the same material as the side walls. It is easy to put medical devices into the space since it forms a space between bottom wall 1 and top wall 2. It is easy to manipulate since the hand insertion parts are large in opening. It is easy to replace the glove with new one since the drape is provided with the opening for installation of a glove. It is possible to prevent the medical device from being contaminated by contact with the opening when the medical device is put into the space since the medical device supply port is reinforced by the reinforcement member to keep the port open during putting the medical device into the space.

Embodiment 2

Figure 5:
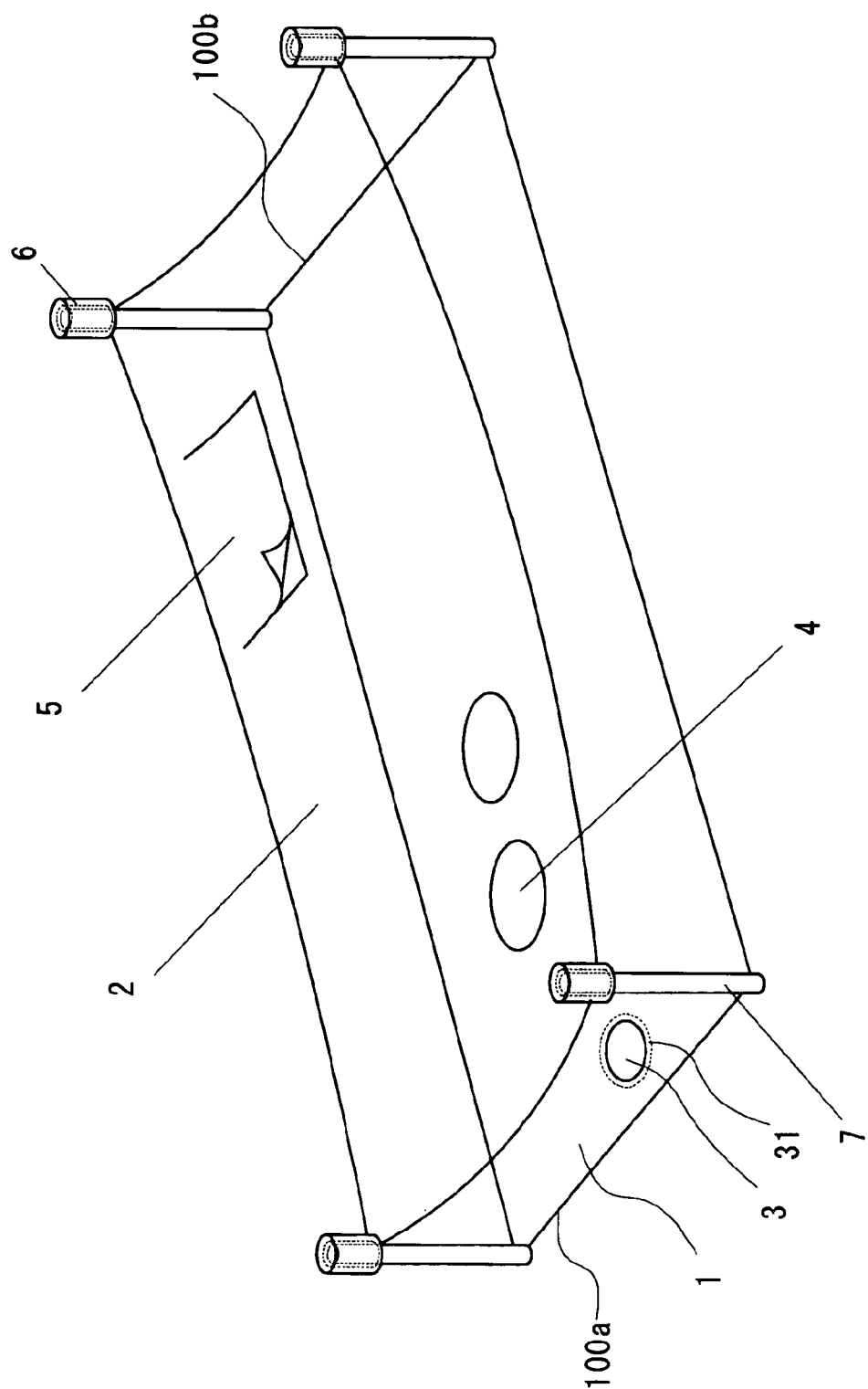
FIG. 5 is a perspective view of a drape for clean operation according to another embodiment of the present invention.
Figure 6:
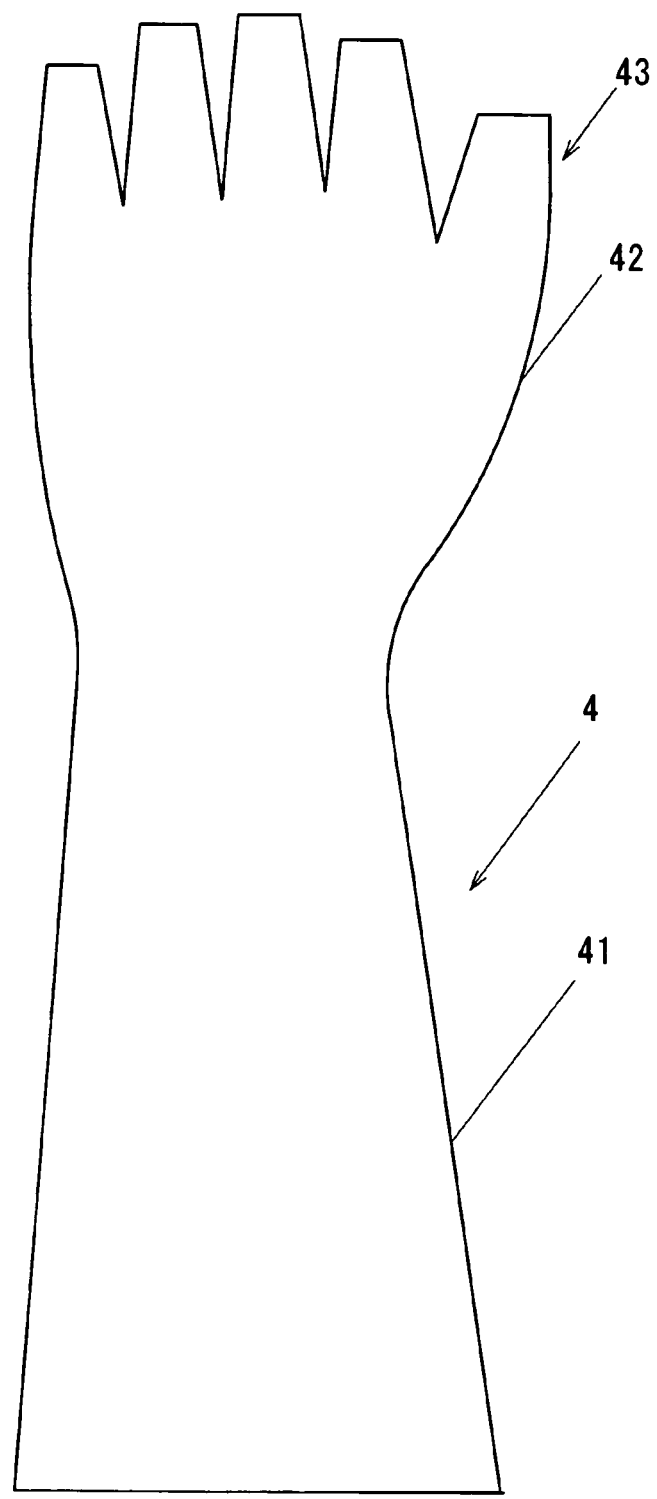
FIG. 6 is an explanatory diagram of hand insertion parts shown in FIG. 5.

FIG. 5 is a perspective view of a drape for clean operation according to another embodiment of the present invention attached to hanging means (four poles), and FIG. 6 is an explanatory diagram of hand insertion parts shown in FIG. 5.

As illustrated in FIG. 5, the drape for clean operation of embodiment 2 is a bag-shaped structure comprising bottom wall 1 and top wall 2 and having a closed proximal end 100a and a closed distal end 100b. The bottom wall 1 is provided with an operation site-revealing opening 3 close to the proximal end 100a of the drape. The top wall 2 is provided with a pair of hand insertion parts 4 (Only openings are shown in the figure) close to the operation site-revealing opening 3. The top wall 2 is also provided with a closed, openable and closable medical device supply port 5 for supplying medical devices required for operations, on the side of the distal end of the drape away from the operation site-revealing opening 3. The medical device supply port 5 may be provided on the side of distal end 100*a* of the drape.

A material for producing the bottom wall 1 and the top wall 2 is a film or a flexible thin sheet made of a transparent plastic material such as polyethylene, polyester, plasticized polyvinyl chloride and polyamides. The bottom wall 1 is preferably made into an opaque sheet to make the operation site invisible.

The medical device supply port 5 may be fixed to the drape by button or MAGIC TAPE (Registered trademark) (not illustrated in the drawings) and is used as a supply port 5 for supplying medical devices such as trays, guide wires or the like. The medical device supply port 5 may be used only for supplying and out the trays and the top wall 2 may be provided with a separate opening for supplying other medical devices as occasion demands.

The bottom wall 1 may be provided with MAGIC TAPE (Registered trademark, not illustrated in the drawings) to make it possible to fix the bottom wall 1 to an auxiliary table for surgical operation. The peripheral part of the operation site-revealing opening 3 is provided with an adhesive tape 31, which adheres to the surrounding of the operation site, so that it enables to prevent movement of the operation site-revealing opening 3 from the operation site and block leakage of the blood out of the operating space and inflow of the open air into the operating space.

The hand insertion parts 4 comprises, As illustrated in FIG. 6, comprises an arm-covering sheath 41 and a glove-shaped hand-covering sheath 42 and are assembled into a glove box. At least the hand-covering sheath 42 is generally made of a plastic material having a good lubricating property in itself, such as polyethylene, polyamide, polytetrafluoroethylene and the like. The hand-covering sheath 42 includes digit-covering sheaths 43 so designed as to have a length that allows the digit-covering sheaths 43 to be easily broken at distal ends thereof by insertion of respective digits and sufficiently expose the digits after being broken. The hand-covering sheath 42 may be improved in lubricating property, for example, by applying silicone oil to an outer surface of the hand-covering sheath 42. The top wall 2 may be provided on the side of the distal end of the drape with a pair of assistant's hand insertion parts (not illustrated in the drawings) similar to the physician's hand insertion parts 4. The bottom wall 1 may be provided with a drain hole (not illustrated in the drawings) close to the edge on the side of the distal end.

The top wall 2 is provided with attaching means 12 for attachment to hanging means 13 (for example, four poles as illustrated in FIG. 5). By attaching the attaching means 12 to the hanging means 7, a space can be formed between the bottom wall 1 and the top wall 2. In case where the hanging means 7 (13) is a pole, the attaching means 12 capable of being used includes strings or pocket-like members which can be fitted on the pole 13.

The above drape is easy to manufacture since it mainly comprises the bottom wall 1 and top wall 2. In case where the material for hand insertion parts is the same material as that of the sidewalls, it is possible to fix the hand insertion parts 4 to the top wall 2 certainly and air-tightly since the hand insertion parts can be easily fusion-bonded to the top wall 2. Further, the top wall is provided with attaching means 12 for attachment to hanging means 13, thus making it possible to a space between bottom wall 1 and top wall 2 by attachment of the attaching means 12 to hanging means 13. Thus, it is easy to put medical devices into the space. Further, it is easy to handle the medical devices.

The invention claimed is:

1. A drape for clean operation being a flexible bag-shaped structure for maintaining a substantially closed operating space around an operation site, said bag-shaped structure comprising:
   a bottom wall; and
   a transparent top wall and having closed proximal and distal ends,
   wherein said bottom wall is provided with at least one operation site-revealing opening close to the proximal end,
   wherein said top wall is provided with at least one pair of hand insertion parts for allowing hands into the operating space at a position close to the at least one operation site-revealing opening, and an openable and closable medical device supply port for supplying medical devices required for operations at a position away from said at least one operation site-revealing opening, and
   wherein said at least one pair of hand insertion parts is formed into a glove box including an arm-covering sheath on the side of the proximal end and a glove-shaped hand-covering sheath on the side of the distal end, said hand-covering sheath having lubricating property and including digit-covering sheaths having a length that allows the digit-covering sheaths to be easily broken at the distal end thereof by insertion of each digit to sufficiently expose the physician's digits to the space after breakage.

2. The drape according to claim 1, wherein said bottom wall is provided with two operation site-revealing openings for exposing an operation site of a patient close to the proximal end of said bag-shaped structure,
   wherein said top wall is provided with a first pair of hand insertion parts for aseptically inserting hands into the operating space, at a position close to one of the operation site-revealing openings on one side of the top wall with respect to the longitudinal axis thereof, and
   wherein said top wall is further provided with a second pair of hand insertion parts for aseptically inserting hands into the operating space, at a position close to one of the operation site-revealing openings.

3. The drape according to claim 2, wherein said top wall is provided with a insertion port for a fluid replacement feeding line, an intravascular probe-loading port and a chemical delivery port on the opposite side of the longitudinal axis of the top wall from the second pair of hand insertion parts.

4. The drape according to claim 2, wherein said top wall is provided with a disposal bag on the opposite side of the longitudinal axis of the top wall from the first pair of hand insertion parts, and
   wherein said top wall is provided with a closable opening for installation of a glove between the disposal bag and the first pair of hand insertion parts.

5. The drape according to claim 1, wherein said operation site-revealing opening is provided with adhesive sealing means around the peripheral part thereof, to prevent displacement of the operation site-revealing with respect to the operation site.

6. The drape according to claim 5, wherein said sealing means is adhesive tape.

7. The drape according to claim 5, wherein said top wall is provided with a disposal bag on the opposite side of the longitudinal axis of the top wall from the at least one pair of hand insertion parts, and
   wherein said top wall is provided with a closable opening for installation of a glove between the disposal bag and the at least one pair of hand insertion parts.

8. The drape according to claim 1, wherein said at least one pair of hand insertion parts is arranged adjacently and fusion-bonded at adjoining parts thereof located at the opening of the proximal end of the hand insertion parts.

9. The drape according to claim 1, wherein said top wall is provided with a first pair of hand insertion parts and a second pair of hand insertion parts, each pair of hand insertion parts being fusion-bonded to each other at the opening of the proximal end of the at least one pair of hand insertion parts.

10. The drape according to claim 1, wherein said top wall is provided with a disposal bag on the opposite side of the longitudinal axis of the top wall from the at least one pair of hand insertion parts, and wherein said top wall is provided with a closable opening for installation of a glove between the disposal bag and the at least one pair of hand insertion parts.

11. The drape according to claim 1, wherein said medical device supply port is reinforced by a reinforcement material in order to keep the open state of said medical device supply port during carrying any medical device.

12. The drape according to claim 11, wherein said top wall is provided with means for fixing the drape to form a space between said top wall and said bottom wall.

* * * * *